United States Patent [19]

Diez de Aux

[11] 4,043,040

[45] Aug. 23, 1977

[54] DENTAL DOWEL PIN SETTING APPARATUS

[76] Inventor: Alfonzo Diez de Aux, 74 James Gray Drive, Willowdale, Ontario, Canada

[21] Appl. No.: 568,112

[22] Filed: Apr. 14, 1975

[51] Int. Cl.² .................................... A61C 13/00
[52] U.S. Cl. ........................................... 32/11
[58] Field of Search ............................ 32/11, 70, 71

[56] References Cited

U.S. PATENT DOCUMENTS

| | | | |
|---|---|---|---|
| 2,836,849 | 6/1958 | Humphrey | 32/11 |
| 3,552,018 | 1/1971 | Zahn | 32/11 |
| 3,650,032 | 3/1972 | Kestler | 32/11 |
| 3,717,933 | 2/1973 | Charron | 32/11 |

*Primary Examiner*—Robert Peshock
*Attorney, Agent, or Firm*—G. James M. Shearn

[57] ABSTRACT

The positioning of dental dowel pins for setting in the die material as it hardens in a tooth cavity of an impression is facilitated by providing a base with a clamp for removably securing the impression thereon and support structure to support a holder for a selected number of dowel pins in individually adjustable positions, and is further facilitated by providing that the apparatus can be used to move the pins out of setting position to allow access or removal of the impression and may thereafter be returned to the predetermined setting position.

5 Claims, 13 Drawing Figures

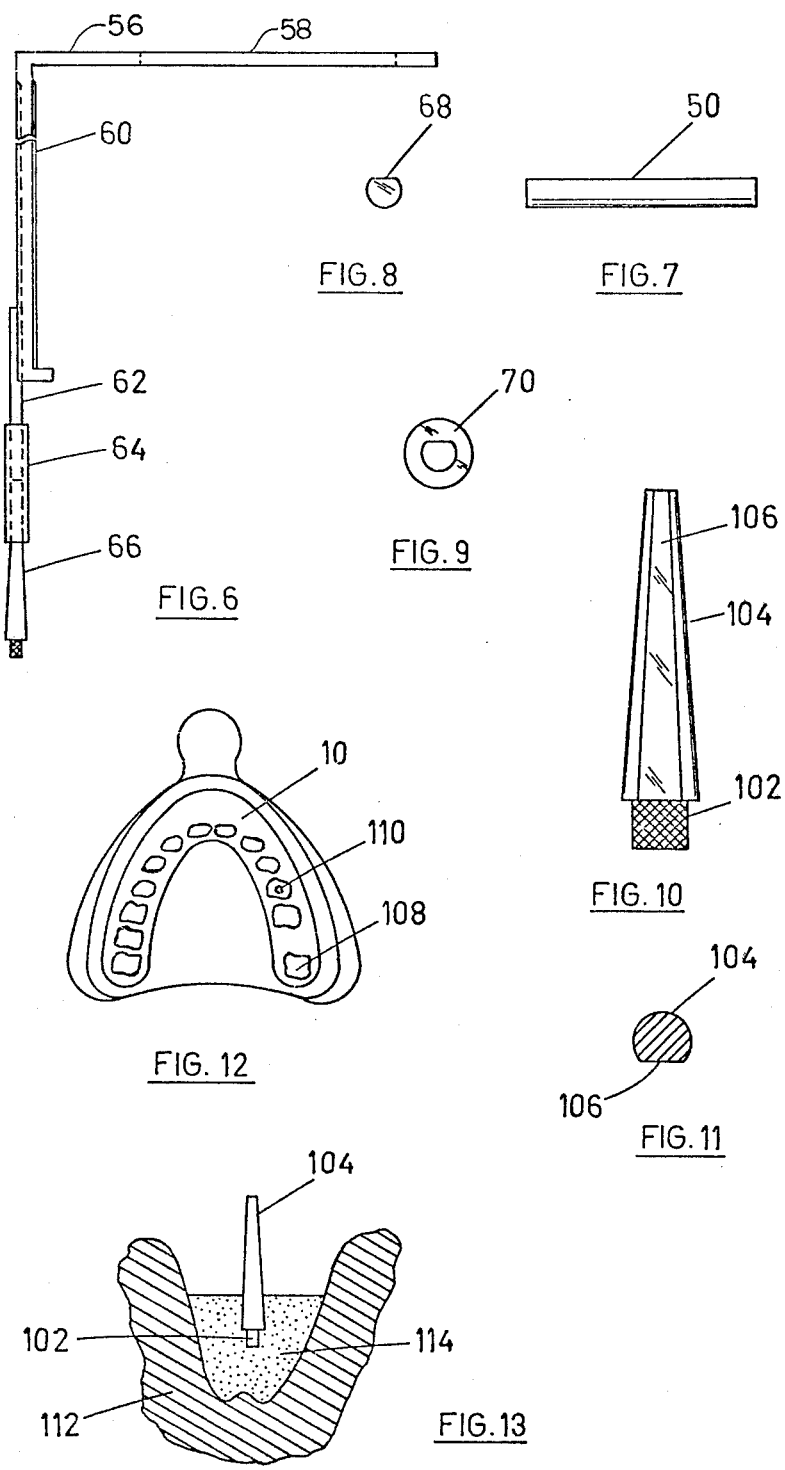

DENTAL DOWEL PIN SETTING APPARATUS

This invention relates to dental apparatus for positioning of dowel pins for setting them in die stone in tooth impressions.

The steps and procedures in preparing artificial teeth are numerous and varied. However, most techniques involve the preliminary steps of forming a negative impression, in pliable material, of a patient's teeth in the patient's mouth and later making a positive replica of the tooth or teeth, called a die, by filling cavities of the negative impression with a die material, commonly called plaster or stone, which is fluid when applied and which hardens in the impression.

In later stages of the procedures it is often desirable to separate (such as by sawing) one tooth die from the remainder of the model of the patient's mouth. In order to permit the separated tooth die to be replaced in its original relative position and orientation the tooth dies are provided with a dowel pin, the shank of which is imbedded in the die material as it hardens in the impression. The shaft of the dowel pin is left projecting from each tooth die and later a second pouring of plaster or other hardenable material is poured over the shaft of the pins to form a foundation with the shafts of the dowel pins imbedded therein. When the separated tooth die is removed to be worked on its is easily replaced in its exact position and orientation by re-inserting the dowel pin in its hole in the foundation material.

Dowel pins commonly used in the industry have a shank end which may be knurled so that it may be set securely in the tooth die material, and a shaft end which usually is a smooth, tapered, truncated conical shape, thickest at its shank end so as to allow it to easily be withdrawn from the foundation material as previously mentioned. In addition these dowel pins usually have a flat side on the shaft, rather than being perfectly circular in cross section, so that the pin and the attached tooth can only be replaced in the foundation in its proper orientation.

Hitherto the setting of the shank end of the dowel pins in the tooth dies has usually been performed manually and the task has been troublesome, time consuming, inaccurate, and requiring of intricate manipulation and judgement by the technician.

It should be understood that one pin is set for each tooth die which is to be worked on. This may mean as many as fourteen in a single impression.

One method currently used is to hold each dowel pin by a piece of wire, attached to or wrapped around the pin, the free ends of which may be pierced into the wall material of the impression to hold the pin in position while the die material hardens around the shank. This however is an imprecise method difficult to execute when many pins are involved and is subject to the limitation that the pins and wire must be in place (and in the way) while the die material is poured into the impression or else pin must be positioned in the impression after the impression cavity is filled and covered with die material.

In addition it is difficult to be sure the pins will all be aligned substantially parallel to each other and at approximately the same height as is desirable. Even after they are positioned by this method the pins, being supported by thin sires, are subject to accidental disturbance or dislocation.

It is therefore an object of this invention to provide apparatus which will aid in more accurately and more firmly positioning dowel pins while they are set in die material.

It is an additional object of this invention to provide apparatus which will allow the adjustable positioning of several pins in an impression, allow withdrawal of pins from the impression to permit the technician to work on the impression and/or pour die stone into the impression cavities, and then allow the accurate relocation of the pins in the poured impression.

It is an additional object of this invention to provide apparatus which will afford the operator more convenient and time saving means to position pins while they are set in die material and allow the operator to work on more projects in a given time.

Accordingly, to achieve these and other advantages and objects the present invention provides apparatus for use in setting the shank of dowel pins in tooth dies made from tooth impressions which apparatus comprises a base, securing means mounted on said base for securing an impression thereon, pin holding means mounted on said base comprising; a holder, support means mounted on said base for adjustably supporting said holder relative to said impression, prong means held by and extending from said holder, said prong means being held by said holder in horizontally adjustable positions relative to said holder and said prongs having means thereon for releasably attaching dowel pins to extend therefrom with said shank in said impression.

The invention will be better understood from an explanation of one embodiment contained in the following description and drawings in which;

FIG. 6 is an elevation view of the apparatus in FIGS. 4 and 5 with a dowel pin attached thereto.

FIG. 7 is a side view of part of the structure for supporting dowel pins.

FIG. 8 is a cross sectional view of the piece in FIG. 7.

FIG. 9 is a plan view of part of the structure of FIG. 1.

FIG. 10 is an elevation view of a dowel pin.

FIG. 11 is a cross sectional view of the dowel pin in FIG. 10.

FIG. 12 is a plan view of a typical impression.

FIG. 13 is a typical cross section view of an impression with die stone and a dowel pin positioned therein.

Figures 1, 2:
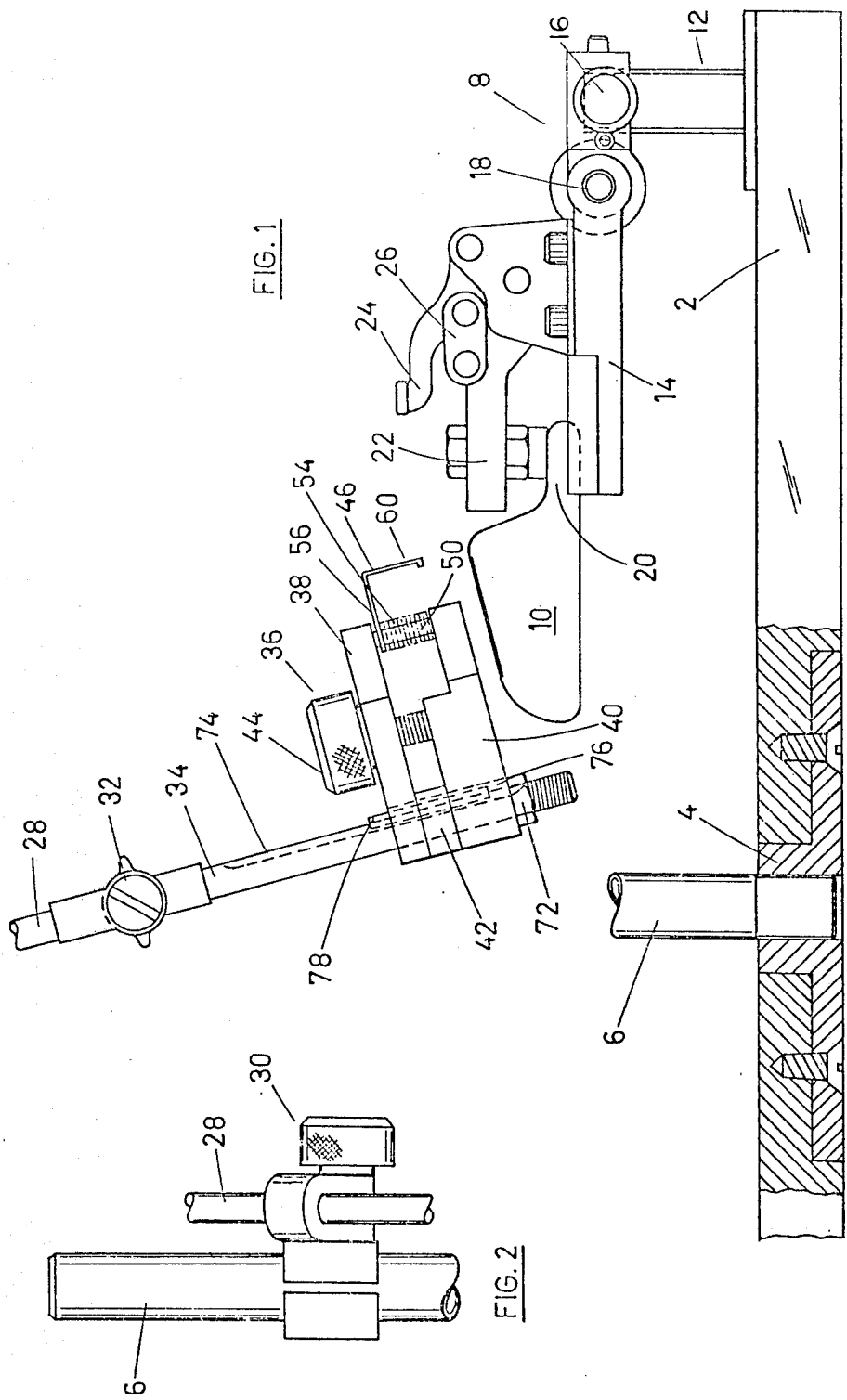
FIG. 1 is an elevation view showing the relative positions of means for supporting an impression and means for supporting dowel pins relative thereto.
FIG. 2 is an elevation view of part of the support structure.

The type of dowel pins commonly used in the industry and contemplated for the hereinafter described embodiment of the invention are illustrated in elevation view in FIG. 10 and in horizontal cross sectional view in FIG. 11 in which the shank portion is shown at 102 and the shaft portion at 104, the latter having a flattened side 106. Note that the shaft is tapered the widest part being near the shank and the narrowest part being at the opposite end.

A typical impression from which dental work of the nature referred to is currently done is illustrated in FIG. 12 in which the impression material 10 has individual tooth cavities such as typified by 108. For illustrative purposes a flat sided dowel pin is shown at 110 in one of the tooth dies in the impression.

FIG. 13 shows, in cross section, the impression material 112 having therein a cavity partially filled by stone material 114 which hardens to form a die of the individual tooth and has imbedded therein a dowel pin of which the shank 102 is buried and the shaft 104 is projecting substantially vertically upwards.

In the illustrated embodiment of the invention FIG. 1 shows a flat horizontal base 2 which may have any horizontal dimension or shape.

Mounted centrally in the base 2 by means of a threaded insert 4 is a cylindrical column 6 extending vertically upwards above the base.

Also mounted on said base but spaced from the column 6 and preferably located near the edge of the base is a securing means generally indicated by 8 by which a mouth impression 10 can be secured in a fixed position relative to the base. In the securing means shown a post 12 mounted on the base supports a cantilever arm 14 which is releasably held on the post by a set screw 16. The cantilever arm is adjustable relative to the horizontal by a joint 18 which may be tightened by another set screw or similar device to hold the arm 14 rigid.

The impression 10 is provided with a handle 20 by which it is firmly held in the securing means by being clamped between the arm 14 and the upper jaw 22 of the clamp mechanism.

The lever 24 and linkage 26 provide means by which the handle may be firmly clamped in or released from the securing means. The exact specification of the clamping mechanism is not given herein in detail since any similar clamping device which holds the impression firmly in position would serve the purpose.

FIG. 2 illustrates an upper portion of the central column 6 having attached thereto a first support arm 28 by means of a double clamp and set screw mechanism generally referred to as 30 by which the support arm 28 may be adjustably clamped to the column 6 in any position or orientation.

Figure 3:
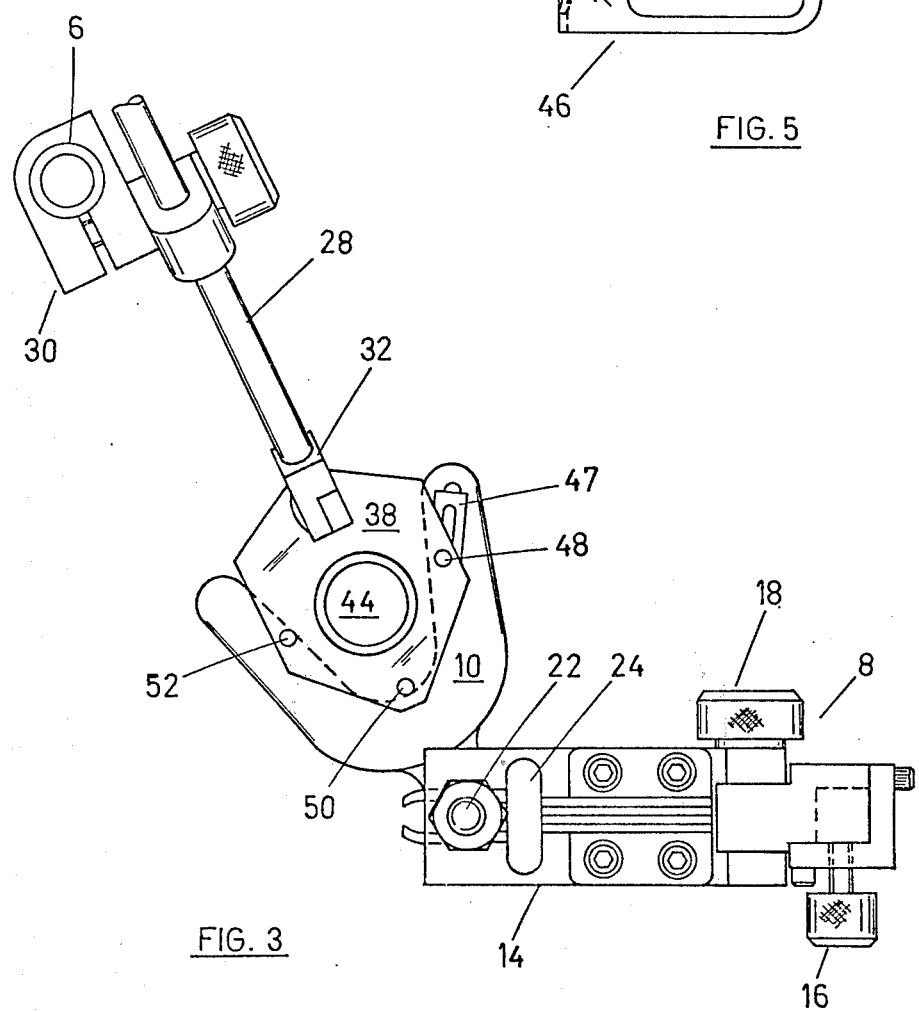
FIG. 3 is a plan view showing the relative position of means for holding an impression and means for supporting dowel pins relative thereto.

FIG. 3 illustrates the structure of FIG. 2 in its relative position to the securing means 8 and in addition an impression 10 is illustrated clamped in the securing means.

As shown in FIGS. 1 and 3 the first support arm 28 terminates in a pivotal elbow joint 32 from which extends a second support arm 34 best shown in FIG. 1. The pivotal elbow joint 32 allows the support arms 28 and 34 to be set at any desired angle to each other (within the plane defined by the motion of the pivot joint) and tightened or secured in that position.

Mounted on the lower end of the second support arm 34 is a holder generally indicated at 36 comprising an upper plate 38 and a lower plate 40 spaced apart by a spacer 42 all of which have a hole therethrough accommodating the arm 34. The upper plate 38 and a lower plate 40 may be urged together by means of a tightening screw 44 which passes through the upper plate and is threadably engaged to the lower plate as illustrated in FIG. 1. The holder is designed to hold one or more prongs, typified by 46, extending outwardly and downwardly from the holder. It is the purpose of these outwardly and downwardly extending prongs to provide a positioning support for the dowel pins to be set in the desired location in relation to the impression 10.

Although only one prong is illustrated in FIG. 1, (and a different prong 47 in FIG. 3), the device can have a series of such prongs all radiating from 3 essentially upright rods 48, 50 and 52 respectively positioned as illustrated in FIG. 3. Where as many as 14 dowel pins are to be set they could be allocated 4 to each of the rods 48 and 52 and 6 to the rod 50 respectively.

Although the illustrated embodiment has 3 rods it should be understood that a different number of rods located at a different number of stations could be used subject to design limitations. For instance if one rod was provided for each prong there would be difficulty in locating as many as 14 stations in the space provided by a holder structure such as 36.

In addition the exact shape of the plates 40 and 38 of the holder is not critical but it is convenient to arrange the rods or stations 48, 50 and 52 so that their relative locations approximate a U-shaped curve reflecting the general shape (although it might be smaller) of the usual impression of a set of teeth.

Referring to FIG. 1 again, where more than one prong such as 46 is to be used they may be positioned on the same rod and be separated by washers each as shown at 54 inserted between the prongs themselves and between the prongs and the plates 38 and 40.

Figure 4:
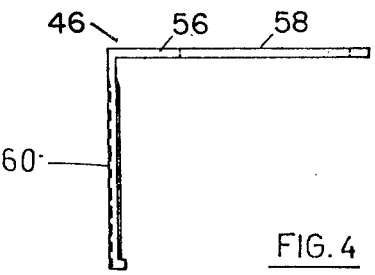
FIG. 4 and FIG. 5 are elevation and plan views of part of the structure for supporting the dowel pins.
Figure 5:
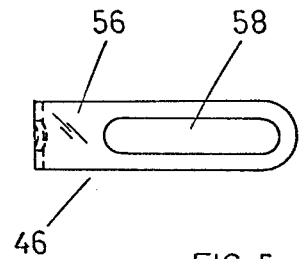

A prong such as 46 is illustrated in FIGS. 4 and 5 in which the horizontal portion 56 has an elongated slot 58 cut therein through which passes the rod 50. It will be understood that the elongated slot will allow the downwardly projecting portion 60 of the prong to be adjusted closer or further away from the holder depending on the position of the tooth impression cavity in which the dowel pin is to be set and the general shape of the mouth impression on which the technician is working. Furthermore the horizontal positioning of the dowel can be adjusted by rotational movement of the prong about its rod 50.

Means for suspending the dowel pin from the prong is illustrated in FIG. 6 in which a wire 62 is attached by welding or soldering or other suitable means to the lower end of the downward projecting portion 60 of the prong. A flexible tubular member 64, such as might be cut from a piece of hollow plastic tubing of appropriate diameter, is tightly fitted over the end of the wire 62 and held in position by friction. The lower half of the tube or sleeve receives in its lower portion the narrow end of the dowel pin 66 in a similar tight friction grip so that the dowel pin is caused to suspend substantially vertically downwards with its shank end lowermost as is normally desirable when the dowel pin is being set in die stone in an impression.

To facilitate adjustment of the individual prongs and the attached dowel pins the rods such as 48, 50 and 52 are constructed as illustrated in FIGS. 7 and 8, being generally cylindrical with one flattened side 68 by which the rods my be held in said holder plates without rotation. The washers 54 previously mentioned are constructed as illustrated in FIG. 9 with a corresponding flattened side so that where there is more than one prong on a rod they are separated by a washer such as 54 which is restricted from rotational movement by the flat side 70 which corresponds to the flat side 68 of the rod. Thus when any given prong is move longitudinally or rotationally with respect to the rod its movement will be isolated from adjoining prongs by washers such as 54 which are prevented from moving with that prong and therefore there will be little or no inclination for other prongs mounted on the rod to move with the prong being adjusted. Therefore adjustment of each prong in turn is facilitated.

Of course because the prongs will be spaced at different heights on the rod as illustrated in FIG. 1 it will be necessary to have some means of compensating so that the ends of the dowel pins are at substantially the same height around the impression. This can be effected by having the wire extension 62 of predetermined different lengths to be selected depending on the position of the prong on the stack in the holder.

It will be understood that the holder should be designed so that the thickness of the spacer 42 bears an appropriate relation to the height of the stack of washers and prongs being held between the plates 38 and 40. Thus where fewer prongs are supported at the pins on the sides at 48 and 52 the spacing between the plates at that point need not be as great as the spacing at the position 40 and this configuration is illustrated in FIG. 1. Furthermore when the technician is working on fewer than a full set of teeth it may be appropriate to set some dummy prongs or spacers so that the space on the rods between the plates 38 and 40 is maintained thereby assuring that when the tightening screw 44 is tightened all of the prongs will be firmly held in their desired pre-set position.

In the illustration of FIG. 1, the holder is shown in a position on the lower end of the arm 34 approximately in the position for setting of a pin in a tooth cavity in the impression. However, in the procedure contemplated it is often desirable to be able to determine the position of the dowel pins while the cavities or the impression are empty and then be able to remove the impression to pour the die stone and possibly to place it on a vibrating table to be sure that the cavity is completely filled with the die stone material and thereafter to be able to reset the dowel pin shanks in the previously determined desirable position in the impression. Therefore to facilitate this type of procedure the holder assembly 36 is movable on the arm 34 so that it can slide up the arm towards the position of the elbow joint 32 and back again. The arm 34 is provided with an adjustable lower stop position provided by means of a nut 72 which may be threaded on to the lower end of the arm 34 and adjusted up or down to set the desired lower setting position of the holder. Furthermore, in order to fix the orientation of the holder and therefore the position of the dowel pins which it supports in the proper relation to the impression cavities the mounting of the holder on the arm 34 is provided with some guide means such as keyway slots 74 and 76 in the arm 34 and the holder assembly 36 respectively and a key 78. This will allow the movement of the holder aforementioned but will maintain the desired orientation when the holder is in the setting position illustrated in FIG. 1. Of course other means could be used such as aflat sided arm 34 and a corresponding flat sided hole in the holder assembly members depending on what is considered convenient for purposes of design and manufacture.

Thus by use of apparatus such as the illustrated embodiment of the invention a technician may secure the impression in the securing means 8 as illustrated in FIGS. 1 and 3 and then by means of the support structure of the column 6, the adjustable clamping means 30, the first support arm 28 and the adjustable pivot elbow 32, and the second support arm 34 he may adjust the location of the holder 36 relative to the impression approximately as illustrated in FIG. 3. Then with the appropriate number of dowel pins depending from prongs such as 46 and with the holder assembly 36 in the lower setting position as illustrated in FIG. 1 he may adjust and fix the dowel pin shanks in the desired location in the cavities of the impression where he will want them to be set in the die stone.

Having set the pins in the desired location relative to the cavities of the impression he may then raise the holder with its attached prongs and dowel pins out of the way by sliding the holder up the arm 34 (where desired he may have some convenient means to hold the apparatus in that position) and he may then remove the impression, if he wishes, by loosening the said screw 16 and removing the impression still securely clamped between the cantilever arm 14 and the upper clamp jaw 22. He may then work on the impression or pour the die stone material into the cavities or apply the impression to a vibrating table to assist filling of the cavities with die material as he pleases. Then having filled the impression with die stone material he may return it to its same position by reassembling the securing means and tightening the said screw 16. The dowel pins may then be re-positioned in the desirable location in the cavity and in the die stone material by moving the holder assembly 36 down the shaft 24 to its previously determined setting position as illustrated in FIG. 1 thus returning the shanks of the dowel pins to their previously determined position in the impression.

Although the foregoing description has dealt with a single impression in a single securing means and a single support structure holder and set of prongs it should be understood that the invention could be used in a laboratory where several projects are being worked on at once. For instance the central column 6 could support numerous adjustable support arms each supporting a holder assembly such as 36 with prongs and dowel pins attached thereto and each cooperating with one of a series of securing means such as 8 stationed at convenient intervals around the periphery of a base such as 2 surrounding the central column 6.

What I claim as new and desire to protect by Letters Patent of the United States is:

1. Dental apparatus for setting the shank end of dowel pins in tooth dies made in an impression comprising:
   a base;
   securing means mounted on said base adapted to clamp said impression upward facing in a selected position;
   a column spaced from said securing means and upstanding from said base;
   a support arm mounted to extend from said column and directionally adjustable relative to said column;
   a holder mounted on said support arm, and adjustable as to spacial orientation thereby, said holder having an upper plate, a lower plate, a rod extending between said plates substantially normal thereto, and means for tightening said plates towards each other;
   a plurality of prongs mounted on said holder each prong having a first portion extending outwardly and a second portion extending downwardly from said first portion substantially normal thereto, said first portion of said prong having an elongated slot receiving said rod therethrough;
   said upper plate and lower plate of said holder being positioned apart to form an adjustable space therebetween and being adapted to clamp said prongs therebetween upon operation of said tightening means;
   means adapted to suspend a dowel pin downwardly extending from said second portion of said prong.

2. Dental apparatus as claimed in claim 1, in which a plurality of said prongs are separated from each other by washers, and in which said rod and said washers have a non-circular cross-section adapted to resist rotation of said washers about said rod.

3. Dental apparatus as claimed in claim 2, in which said support arm has a first portion extending outwardly from said column and a second portion attached to extend from said first portion, and in which said holder is mounted on said second portion and movable thereon between a first position adjacent to said impression and a second position removed therefrom.

4. A dental apparatus as claimed in claim 3, in which the second portion of said support arm is pivotally attached and directionally adjustable relative to said first portion.

5. Dental apparatus as claimed in claim 4, in which said impression securing means includes means to adjust the position of said clamped impression and includes means for detachment of said clamped impression for removal thereof and for replacement thereof in said position.

* * * * *